United States Patent [19]
Garrity et al.

[11] Patent Number: 5,853,724
[45] Date of Patent: *Dec. 29, 1998

[54] DAMPENING OF AN IMMUNODOMINANT EPITOPE OF AN ANTIGEN FOR USE IN PLANT, ANIMAL AND HUMAN VACCINES AND IMMUNOTHERAPIES

[75] Inventors: Robert R. Garrity, Middletown; Peter L. Nara, Frederick, both of Md.; Jaap Goudsmit, Amsterdam, Netherlands

[73] Assignee: The United States of America as represented by the Department of Health and Human Services, Washington, D.C.

[*] Notice: The term of this patent shall not extend beyond the expiration date of Pat. No. 5,585,250.

[21] Appl. No.: 764,575

[22] Filed: Dec. 13, 1996

Related U.S. Application Data

[63] Continuation of Ser. No. 109,934, Aug. 20, 1993, Pat. No. 5,585,250.
[51] Int. Cl.⁶ .......................... A61K 39/00; A61K 39/21; C07K 1/00; C07K 14/00
[52] U.S. Cl. ..................................... 424/184.1; 424/188.1; 424/204.1; 424/288.1; 530/395
[58] Field of Search ............................. 424/184.1, 188.1, 424/204.1, 288.1; 530/395

[56] References Cited

U.S. PATENT DOCUMENTS 5,041,376  8/1991  Gething et al. ...................... 435/172.3
5,585,250  12/1996  Garrity et al. .......................... 435/69.3

OTHER PUBLICATIONS

S. Olofsson, et al.; Vaccines 93.; pp. 183–187; "Peripheral Carbohydrate structures engaged in regulation of antigenic properties of HIV–1 gp120".

A. Bolmstedt, et al.; Journal of General Virology; vol. 73, No. 12, Dec. 1992, pp. 3099–3105; "Carbohydrate determinant NeuAc–Galbeta(1–4) of N–linked glycans modulates the antigenic activity of human immunodeficiency virus type 1 glycoprotein gp120".

P. Simmonds, et al.; Journal of Virology; vol. 164, No. 12, Dec. 1990; pp. 5840–580; "Analysis of sequence diversity in hypervariable regions of the external glycoprotein of human immunodeficiency virus type 1".

H. Kohler, et al.; Journal of Acquired Immune Deficiency Syndromes; vol. 5, No. 11, Nov. 1992; "Clonal Dominance: Cause for a limited and failing immune response to HIV–1 infection and vaccination".

R. Garrity, et al.; Aids Research and Human Retroviruses; vol. 10, No. SUP1; Aug. 1993; "Introduction of potential N–linked glycosylation sites into the V3 domain of HIV–1 gp120: Effects on virus viability, antigenicity and immunogenicity".

*Primary Examiner*—Lynette F. Smith
*Attorney, Agent, or Firm*—Knobbe, Martens, Olson & Bear, LLP

[57] ABSTRACT

The present invention provides a vaccine that can be administered to a mammal to cause immunoprotection in the mammal against a pathogenic organism that has an immunodominant epitope. The vaccine includes a modified form of the antigen in which the immunodominant epitope is located. In this modified form, the immunodominant epitope is immunodampened by any of a number of techniques. Examples of immunodampening techniques include addition of N-linked glycosylation sites, change of the net charge on the epitope, and substitution with a tolerated sequence. The vaccine also includes a pharmacologically acceptable carrier.

14 Claims, 5 Drawing Sheets

(SEQ. ID NO.: 1)

FIG. 7

| anil-gp41 | WT | 1 | 2 | 3 | 1:3 | 1:4 | 2:4 | 1:2:4 | 1:2:3:4 |
|---|---|---|---|---|---|---|---|---|---|
| V3 Antibody | + | + | + | + | + | + | + | + | + |
| F58/H3 | + | + | + | + | + | + | − | − | − |
| 0.5β | + | + | − | − | + | − | − | − | − |
| 9284 | + | + | + | + | + | + | − | − | − |
| H902 | + | + | + | − | + | − | + | − | − |
| RP135 | + | + | + | − | + | + | + | + | − |

-CTRPNNNTRXRIRIQRGPGRAFVTIGXIGNMRQAHC-
(SEQ. ID NO.: 1)

5,853,724

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( x i ) SEQUENCE DESCRIPTION: SEQ ID NO:1:

```
Cys Thr Arg Pro Asn Asn Asn Thr Arg Lys Arg Ile Arg Ile Gln Arg
1               5                   10                  15
Gly Pro Gly Arg Ala Phe Val Thr Ile Gly Lys Ile Gly Asn Met Arg
            20                  25                  30
Gln Ala His Cys
        35
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

TCCGTATCCA GAATGGATCA GGGAGAGCAT      30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

ATGCTCTCCC TGATCCATTC TGGATACGGA      30

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CCAGGGAGAG CAAATGTTAC AATAGG        26

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

CCTATTGTAA CATTTGCTCT CCCTGG        26

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

ATACAAGAAA AAACATCAGT ATCCAGAGAG        30

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

CTCTCTGGAT ACTGATGTTT TTTCTTGTA        29

( 2 ) INFORMATION FOR SEQ ID NO:8:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

GTATCCAGAA TGGATCAGGG AGAGCA                         26

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

TGCTCTCCCT GATCCATTCT GGATAC                         26

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

TCAGGGAGAG CAAATGTTAC AATAGG                         26

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

CCTATTGTAA CATTTGCTCT CCCTG                          25

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

TCAGTATCCA GAATGGATCA GGGAGA                                          26

( 2 ) INFORMATION FOR SEQ ID NO:13:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TCTCCCTGAT CCATTCTGGA TACTGA                                          26

( 2 ) INFORMATION FOR SEQ ID NO:14:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

GGCAAGTGGT CAAAAGCGGC CGCTAC                                          26

( 2 ) INFORMATION FOR SEQ ID NO:15:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

GTAGCGGCCG CTTTTGACCA CTTGCC                                          26

( 2 ) INFORMATION FOR SEQ ID NO:16:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: cDNA -continued ( i i i ) HYPOTHETICAL: NO ( i v ) ANTI-SENSE: NO ( x i ) SEQUENCE DESCRIPTION: SEQ ID NO:16:

CAGAGAGAAA AAAGATAAGC GGCCGCTGC 29

( 2 ) INFORMATION FOR SEQ ID NO:17:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GCAGCGGCCG CTTATCTTTT TTCTCTCTG 29

( 2 ) INFORMATION FOR SEQ ID NO:18:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

AGAAAAACTA GTTACTTAAC TAGTAGGCCT GAATTCCTCG AGAAGCTTGT CGACGGATCC 60

DAMPENING OF AN IMMUNODOMINANT EPITOPE OF AN ANTIGEN FOR USE IN PLANT, ANIMAL AND HUMAN VACCINES AND IMMUNOTHERAPIES

This application is a continuation of application Ser. No. 08/109,934, filed Aug. 20, 1993, now U.S. Pat. No. 5,585,250.

FIELD OF THE INVENTION

The present invention relates to the manipulation of immune responses. More specifically, immunodampening is used to focus immune effector responses to previously silent or relatively non immunogenic epitopes on disease associated antigens.

BACKGROUND OF INVENTION

Pathogenic agents such as viruses, bacteria, metazoan parasites and human cancers have evolved elaborate strategies to defeat the host immune response. Such strategies often hamper efforts to develop successful vaccines against many pathogenic organisms.

Certain parasites have evolved an intracellular habitat that helps the parasites avoid the effects of antibody. Other parasites like the African trypanosomes use a process called antigenic variation to change the character of their surface coats. Still other pathogens have developed ways to suppress the host's immune response by releasing lymphocytotoxic factors.

According to yet another strategy the pathogen displays an immunodominant epitope that undergoes structural variation or antigenic drift. Early neutralizing antibody and/or cytotoxic T lymphocyte (CTL) responses which are raised against these epitopes represent an attempt by the host's immune system to reduce the titer of the dominant pathogenic phenotype. However, there is a lag-period between the time of infection and the appearance and effect of these immune responses. Moreover, antigenic drift of the immunodominant epitope results in these early neutralizing antibodies or CTL responses becoming ineffective against the pathogen.

The human immunodeficiency virus-1 (HIV-1) has evolved an exquisite strategy that it uses to evade, and so to destroy, the human immune system. None of the vaccine approaches that have been attempted to date have proved successful. One approach at vaccine production has centered on gp120/160 of HIV-1. Neutralizing antibodies can be raised against the dominant V3 domain of gp120/160. However, these neutralizing antibodies are not effective in preventing the continued growth of HIV-1 in vivo. Haigwood et al., *AIDS Research and Human Retroviruses* 6:855–69 (1990), produced a gp120/160 immunogen that did not harbor the dominant V3 domain by deleting the amino acids that comprised the V3 domain. This engineered protein was produced in a non-glycosylated form in yeast, denatured and used to immunize test animals. This approach failed to elicit a more conserved neutralizing response.

The influenza virus hemagglutinin antigen (HA) provides another example of a pathogen-encoded immunodominant antigen that is subject to antigenic drift. Indeed, variation in the antigenic structure of HA correlates with the periodic epidemics of respiratory disease that are caused by this virus. Under experimental conditions, the selective pressures imposed by propagating the virus in the presence of neutralizing antibodies have lead to the emergence of resistant variants. In one example, a mutation at position 63 of HA1 (D to N) resulted in the creation of a three amino acid motif that fit the consensus N-X-S/T. This motif serves as the signal for N-linked oligosaccharide addition to proteins that transit through the endoplasmic reticulum and golgi. The presence of a supernumerary carbohydrate blocked the interaction between the HA protein and the neutralizing antibody. This was confirmed by the finding that propagation of this mutant in the presence of tunicamycin, an inhibitor of N-linked glycosylation, restored antibody binding. Hence, a post-translational modification of a virally encoded epitope can interfere with the binding of neutralizing antibodies.

Gething et al., U.S. Pat. No. 5,041,376, discloses a method for shielding epitopes of proteins by incorporating N-linked oligosaccharide side chains using oligonucleotide mutagenesis. The contemplated use of the N-linked modifications of the proteins is to increase the circulation time of the antigens by decreasing their immunogenicity.

SUMMARY OF THE INVENTION

One aspect of the present invention is a vaccine that can be administered to a human subject to cause immunoprotection in the subject against HIV-1. This vaccine comprises a modified form of gp120/160 of HIV-1, in which the V3 loop of the gp120/160 is immunodampened, and a pharmacologically acceptable carrier for administration to a human subject. Preferably, the V3 loop in the vaccine has a modified amino acid sequence that includes one or more N-linked glycosylation signals that are not present in native V3 loop.

Another aspect of the present invention is a vaccine that can be administered to a mammal to cause immunoprotection in the mammal against a pathogenic organism, wherein the pathogenic organism comprises an antigen with an immunodominant epitope. This vaccine comprises a modified form of the antigen, in which the immunodominant epitope is immunodampened, and a pharmacologically acceptable carrier. Preferably, the carrier comprises a pharmacologically acceptable saline buffer. The immunodominant epitope can, for example, be immunodampened by the addition of carbohydrate moieties to the epitope. When the immunodominant epitope comprises a plurality of amino acids, though, the epitope can be immunodampened by an alteration of these amino acids. In this embodiment, the alteration can comprise an amino acid substitution, and the plurality of amino acids can be substituted with a different plurality of amino acids that are tolerated by human B cells. The different plurality of amino acids can comprise, for example, a linear human B-cell epitope. The plurality of amino acids can also have a native charge, so that the alteration results in a change of the native charge. The alteration can further comprise a deletion of one or more of the plurality of amino acids.

In another embodiment of this aspect of the present invention, the immunodominant epitope includes a binding site for at least one other molecule, and the vaccine additionally comprises at least one other molecule irreversibly bound to the epitope. This other molecule can comprise, for example, an antibody directed against the epitope. The epitope in this embodiment can also comprise a receptor, and the other molecule can comprise a ligand for the receptor. In yet another embodiment of the invention, the immunodominant epitope is an epitope against which the mammal can raise neutralizing antibodies. Such an immunodominant epitope can comprise a plurality of amino acids, and the plurality of amino acids can be changed without affecting the survival ability of the pathogenic organism, thereby allowing the plurality of amino acids to change by genetic drift over a plurality of generations of the pathogenic organism.

The vaccine of the present invention can confer immunoprotection against a number of pathogenic organisms, including fungi, protozoa, bacteria, and viruses, such as influenza virus and HIV. In one embodiment, the pathogenic organism is HIV-1, and the immunodominant epitope is the V3 loop of gp120/160 of HIV-1. This epitope can further comprise a plurality of amino acids that have been altered to include additional N-linked glycosylation signals.

Yet another aspect of the present invention is a method of immunizing a mammal against a pathogenic organism that comprises a native antigen with an immunodominant epitope. This method includes the step of administering to a mammal a vaccine that comprises a modified form of such a native antigen in which the immunodominant epitope is immunodampened. Preferably, this method additionally includes the step of administering native antigen to the mammal prior to administering the vaccine. When administering such native antigen, a vector that encodes the native antigen and expresses the native antigen in the mammal is also preferably administered to the mammal.

A further aspect of the present invention is a method of making a vaccine that can be administered to a mammal to cause immunoprotection in the mammal against a pathogenic organism that comprises an antigen with an original immunodominant epitope. This antigen also comprises a plurality of amino acids, including a subset of amino acids that comprise the original immunodominant epitope. This method comprises the steps of: 1) obtaining a polynucleotide sequence encoding the plurality of amino acids that includes the subset of amino acids comprising the original immunodominant epitope; 2) modifying the polynucleotide sequence so as to encode a modified immunodominant epitope that comprises a different subset of amino acids than the original immunodominant epitope; 3) expressing the polynucleotide sequence produced as a result of the modifying step, thereby producing a modified antigen that includes the modified immunodominant epitope, whereby the modified immunodominant epitope is immunodampened relative to the original immunodominant epitope; and 4) formulating a vaccine composition that includes the modified antigen and a pharmacologically acceptable carrier.

In this further aspect of the present invention, the modifying step can comprise producing a modified polynucleotide sequence that encodes at least one amino acid substitution in the original immunodominant epitope. This modified polynucleotide sequence can encode, for example, a modified immunodominant epitope that is tolerated by human B cells. The modified immunodominant epitope can, for example, be a linear human B-cell epitope. In the modifying step, the subset of amino acids that comprise the original immunodominant epitope can also have a native charge, and the modifying step can produce a modified polynucleotide sequence that encodes a modified immunodominant epitope that has a different charge than the native charge. In another embodiment, the modifying step can comprise producing a modified polynucleotide sequence that encodes at least one amino acid deletion in the original immunodominant epitope.

Another aspect of the present invention is a method of making a vaccine that can be administered to a human subject to cause immunoprotection in the subject against HIV-1. This method comprises obtaining gp120/160 antigen of HIV-1; treating the gp120/160 antigen by exposure to thrombin so as to cleave the gp120/160 antigen; and formulating a vaccine composition that includes the thrombin-treated antigen and a pharmacologically acceptable carrier. Preferably, the 9238 site of the gp120/160 antigen used in this aspect of the invention remains intact during the treating step of this method.

Yet another aspect of the present invention is a vaccine that can be administered to a human subject to cause immunoprotection in the mammal against HIV-1. This vaccine is produced by obtaining gp120/160 antigen of HIV-1; treating the gp120/160 antigen by exposure to thrombin so as to cleave the gp120/160 antigen; and formulating a vaccine composition that includes the thrombin-treated antigen and a pharmacologically acceptable carrier.

BRIEF DESCRIPTION OF FIGURES

FIG. 7 shows the primary sequence of the HXB2 V3 domain, the epitope targets of antibody reagents used to assess the antigenicity of recombinant envelope proteins, and a summary of the antibody binding data derived from Western analysis. A "+" indicates staining by the antibody reagent while "-" indicates no detectable staining.

DETAILED DESCRIPTION OF THE INVENTION

A. Definition of Terms

Figure 1:
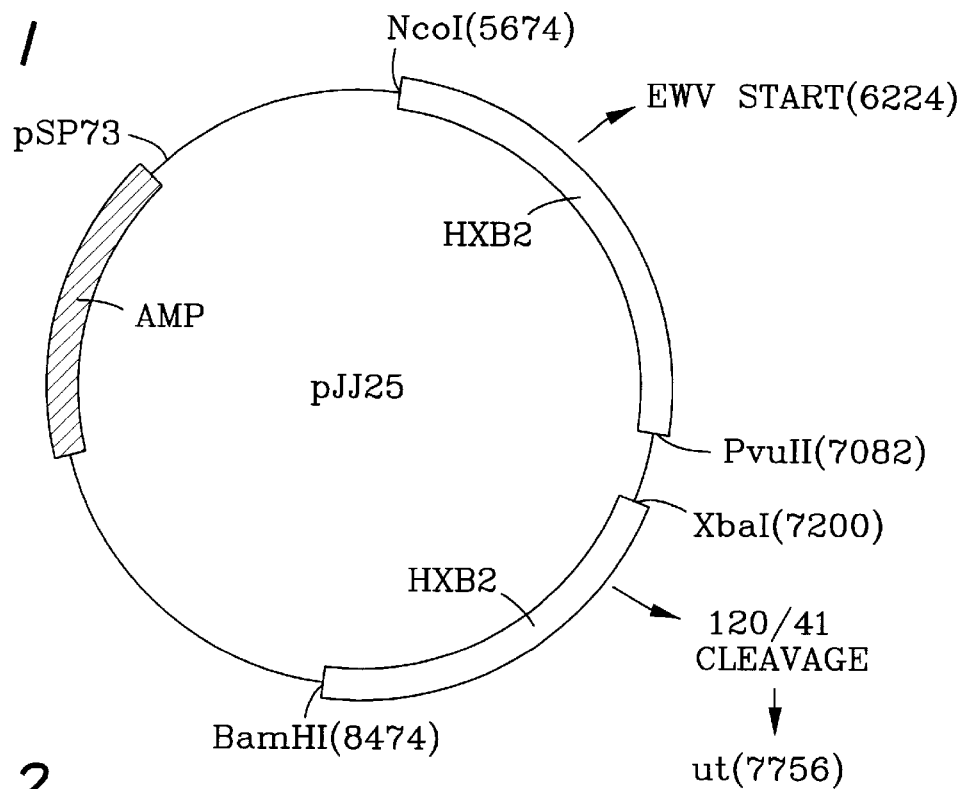
FIG. 1 is a schematic diagram of plasmid pJJ25.
Figure 2:
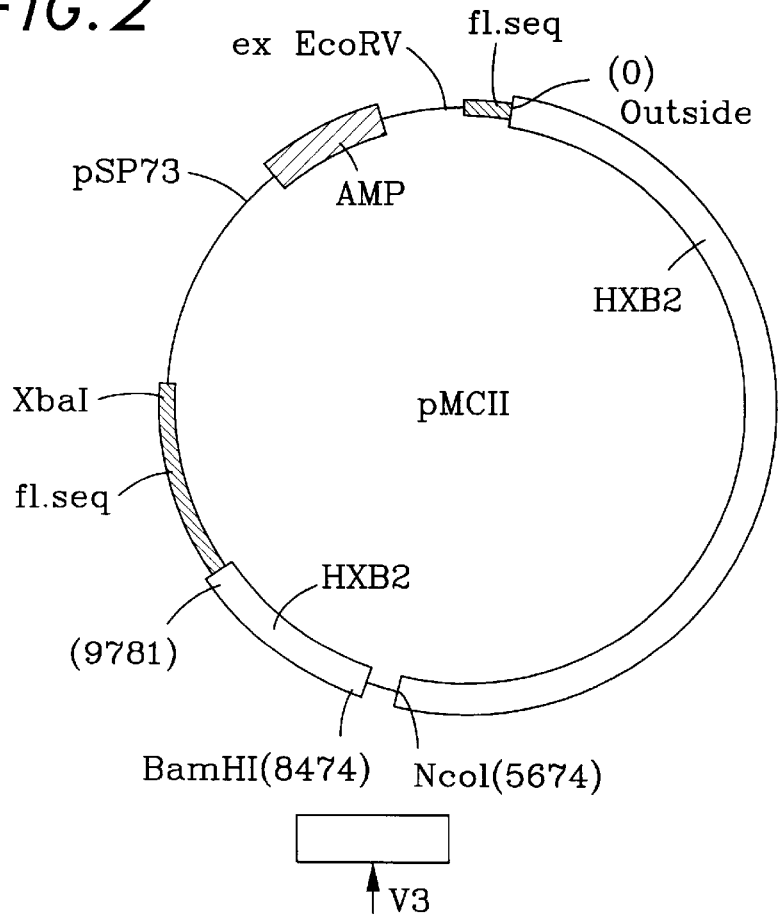
FIG. 2 is a schematic diagram of plasmid pMCII.
Figure 3:
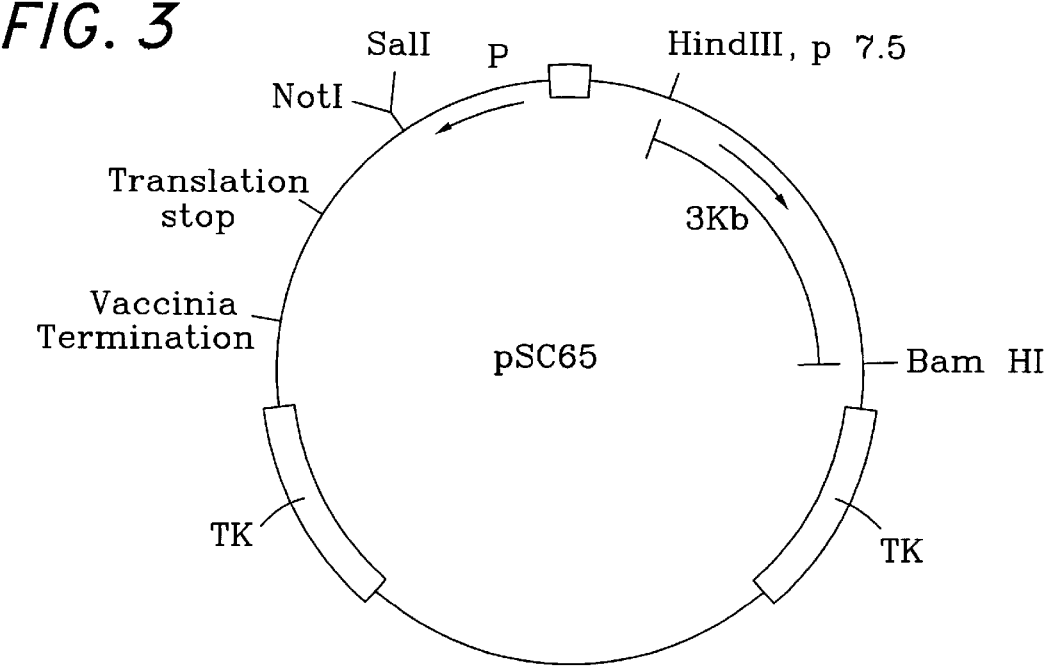
FIG. 3 is a schematic diagram of plasmid pSC65.
Figure 4:
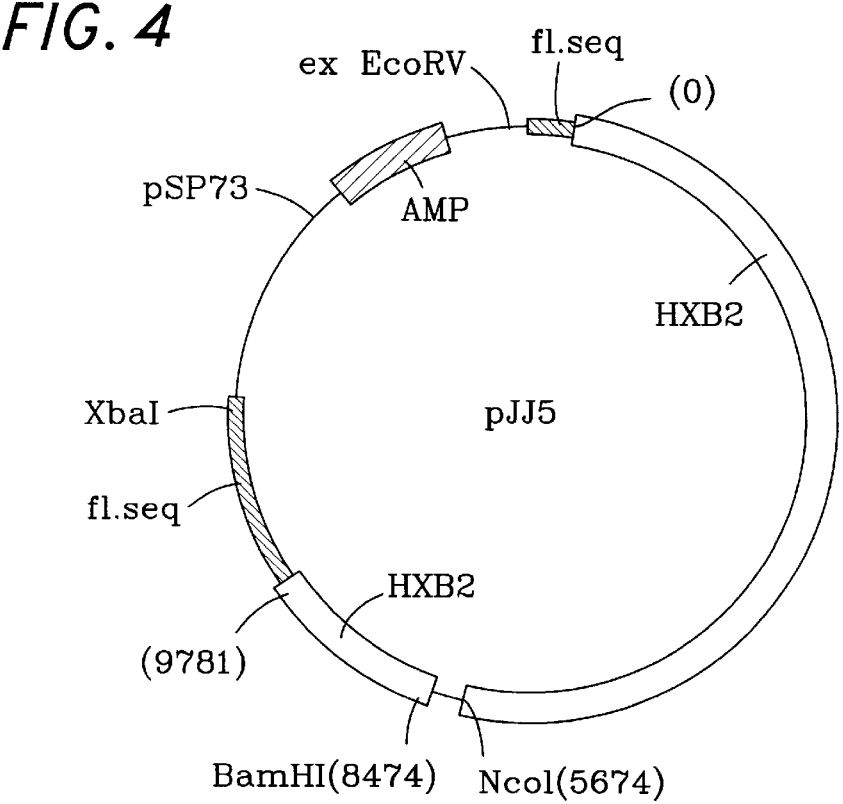
FIG. 4 is a schematic diagram of plasmid pJJ5.
Figure 5:
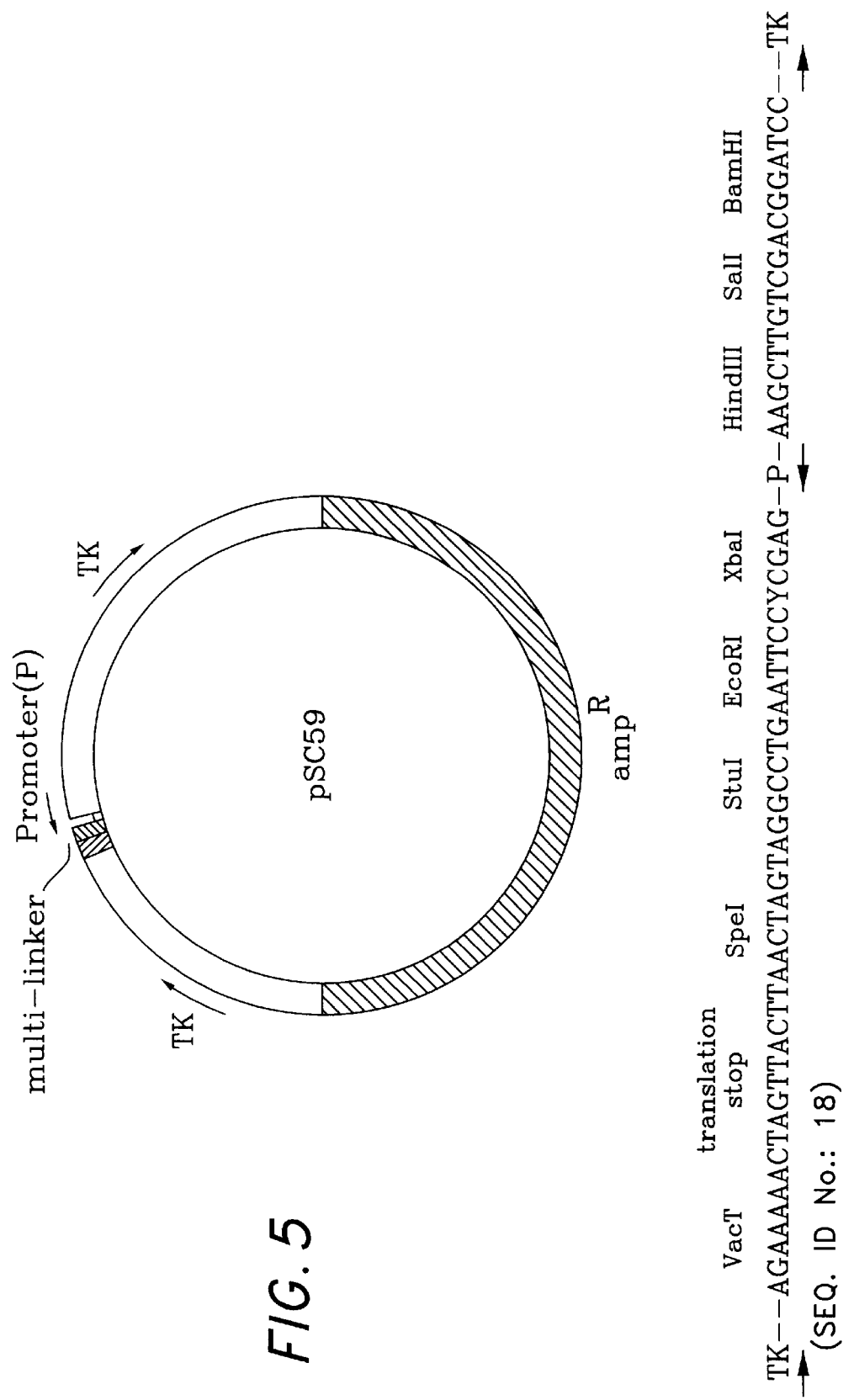
FIG. 5 is a schematic diagram of plasmid pSC59.

As used herein, the term "Immunoprotection" refers to the ability to obviate infection and/or lead to protection, prevention or attenuation of disease caused by an organism;

"Immunodominant epitope" shall mean the epitope on an antigen that selectively provokes an immune response in a host organism to the substantial exclusion of other epitopes on that antigen;

"To immunodampen an epitope" shall mean to modify that epitope so as to substantially prevent the immune system of the host organism from producing antibodies against that epitope; however, immunodampen does not include the complete removal of the epitope.

The term "gp120/160" is used herein to refer to the gene that encodes the membrane-bound gp160 and the free gp120 derived therefrom, and to either of the gene products.

Other terms shall be given the meanings as used in connection with this Detailed Description of the Invention.

B. Recombinant Plasmids Used

Various plasmids are described herein in connection with specific examples of methods of making and using the present invention. DeJong et al., in Vaccines 92, Modern Approaches to new Vaccines Including the Prevention of AIDS, Chanock et al. eds., New York (1992), used recombinant plasmids pJJ25 and pMC to facilitate the subcloning of a region containing the third hypervariable domain (V3 loop) of HXB2, HIV-1 gp120/160. Recombinant plasmid pJJ25 carries an NcoI to BamHI HXB2-like fragment (nts 5675–8478) which contains a small PvuII-XbaI stuffer-insertion. Recombinant plasmid pMCII carries a full length infectious HXB2-like genome. Expression vector pSC65, described in Current Protocols in Molecular Biology, Greene Publishing and Wiley-Interscience Supplement 15 (1992), p. 16.17.2, carries an early-late super vaccinia promoter with down stream subcloning sites juxtaposed in the middle of an intact Thymidine Kinase gene. Modified pGEM-1 (Promega Corp., Madison, Wis.) was used as a direct recipient for V3 loop exchange. Plasmid pJJ5 is a complete molecular clone of HXB2 lacking the NcoI-BamHI fragment (nts 5674–8474 of the Los Alamos nomenclature). The plasmid pSC59 is the parent plasmid that was used in the construction of pSC65.

The sequence of HXB2, including a comprehensive restriction map thereof, can be located in GenBank at Accession No. K03455. Further sequence data, showing PvuII and XbaI cleavage sites can be found in GenBank Accession No. M17449.

C. Introduction

We have discovered that immunodampening of an immunodominant epitope of an antigen can result in the production in a host organism of high titer antibodies against non-dominant epitopes on that antigen. Such immunodampened antigens can serve as effective vaccines against organisms that have an antigen with a highly variable immunodominant epitope, such as HIV, influenza viruses, lentiviruses and other viruses.

In one examplary application of our discovery, we have discovered that recombinant gp120/160 proteins of human immunodeficiency virus-1 (HIV-1) that display a supernumerary N-linked carbohydrate in the immunodominant V3 domain exhibit novel antigenic properties. Included among these properties is the inability to bind antibodies that recognize wildtype V3 epitopes. We also discovered that the presence of this supernumerary carbohydrate moiety does not compromise the infectious viability of the HIV-1 recombinant virus. Furthermore, we discovered that test animals immunized with a recombinant virus that directs expression of a V3 mutant gp120/160 protein with supernumerary N-linked carbohydrate moieties showed high titers of antibodies that neutralize infection by wildtype HIV-1 in vitro. Thus, immunodampening of the immunodominant epitopes within the V3 domain of gp120/160 causes the immune response to refocus on other neutralizing epitopes that are located on the same antigen.

D. Identification of Organism

The techniques of the present invention can be used to create effective vaccines against a large number of unrelated pathogenic organisms. The invention is most appropriately applied in organisms that have developed a strategy of evading a host organism's immune response by having an immunodominant epitope that displays a high level of antigenic drift. Such an immunodominant epitope ordinarily takes the form of a plurality of amino acids that can be changed without affecting the survival ability of the pathogenic organism. Examples of such immunodominant epitopes are the V3 domain of gp120/160 of HIV-1 and HA of influenza viruses. Other epitopes likely to exhibit immunodominance are those that are shown to vary considerably over the course of infection, such as the surface antigens of African trypanosomes.

E. Identification of Immunodominant Epitope

The vaccines of the present invention are created by first identifying an immunodominant epitope in a pathogenic organism. The antigen likely to carry an immunodominant epitope can be identified by selecting antigens on the outer surface of the pathogenic organism. For example, most simple organisms, such as fungi, bacteria and viruses have one or two proteins that are exposed on the outer surface of the pathogenic organism. These outer surface proteins are most likely to carry the appropriate antigen. The proteins most likely to carry an immunodominant epitope can be identified in a Western assay in which total protein is run on a gel against serum from an organism infected with the pathogenic organism. Bound antibodies from the serum are identified by labeled anti-antibodies, such as in one of the well-known ELISA techniques.

The immunodominant epitope can be identified by examining serum from a host organism infected with the pathogenic organism. The serum is evaluated for its content of antibodies that bind to the identified antigens that are likely to cause an immune response in a host organism. If an immunodominant epitope is present in these antigens, substantially all antibodies in the serum will bind to the immunodominant epitope, with little or no binding to other epitopes present in the antigen.

As an example of the identification of an immunodominant epitope, the V3 domain of gp120/160 of HIV-1 was identified by others as the immunodominant epitope of HIV-1 by peptide scanning in a competitive assay. Antisera was obtained that neutralized virus in vitro. A series of overlapping peptides was prepared from gp120/160. An excess of each of these peptides was added to the serum serially. Each serum sample was tested for neutralizing activity against HIV-1. It was found that peptides from the V3 domain of gp120/160 eliminated substantially all neutralizing activity of the serum.

F. Immunodampening of Immunodominant Epitope

After an immunodominant epitope has been identified, the immunodominant epitope is immunodampened. Immunodampening can be accomplished in accordance with any of a variety of techniques, as is described hereinbelow.

Introduction of N-linked Carbohydrates

Immunodominant epitopes can be immunodampened by introduction of N-linked carbohydrate residues. In peptide epitopes, this can readily be accomplished by site-directed mutagenesis of the gene coding for the epitope to include additional N-linked glycosylation signals.

The presence of N-linked carbohydrate (CHO) is determined by the primary amino acid sequence of the polypeptide. A triplet amino acid sequence consisting of asparagine, followed by any amino acid, and ending with a serine or threonine (N-X-S/T), where X is any amino acid other than proline or aspartic acid, is believed to be the signal for N-linked CHO additions. Addition of complex carbohydrates, such as those assembled at N-linked sequences is believed to decrease or dampen the immune systems ability to raise antibody to this site. This has been proposed for certain N-linked domains on the influenza hemagglutinin protein. Wiley et al. *Nature,* 289:373–387 (1981). In the case of influenza, CHO additions shield the virus from immune attack. Knowledge, therefore, of the primary amino acid sequence of a given pathogenic glycoprotein, such as proteins seen by the immune system, can be used to site-direct the introduction or removal of N-linked sequences through molecular manipulation. The introduction of these N-linked sites is designed to prevent B-cells from responding to them.

As an example of immunodampening of an epitope by N-linked carbohydrate addition, the immunodominant V3 loop of HIV-1 gp120/160 can be immunodampened by PCR site-directed mutagenesis, as in Example 1.

EXAMPLE 1

PCR Site-Directed Mutagenesis

N-linked glycosylation consensus sites (i.e., amino acids NXT or NXS) were introduced into the V3 loop via PCR site directed mutagenesis by the method of Haguchi, In PCR Protocols, pp. 177–183, Academic Press, San Diego, Calif. (1990), the disclosure of which is hereby incorporated by reference. Briefly, complementary primer pairs were synthesized carrying exact V3 sequences and a desired N-linked mutation. Two partially complementary halves of the V3 region of pMC were amplified by PCR. Reaction 1 included a 5' primer which overlapped a unique, naturally occurring PvuII site (nts 7082–7087) which is just proximal to the V3 N-terminal cysteine, and a 3' primer including an N-linked in frame mutation. Reaction 2 included a 5' inverted complement to the 3' primer used in reaction 1, and a 3' primer overlapping and including a silent XbaI mutation just proximal to the C-terminal cysteine of the V3 loop (nts 7223–7228). Both reactions were electrophoresed on agarose, cut out from the gel, and the gel slices were centrifuged for 15' in a 1.5 ml costar tube (Amicon). Three μl from reactions 1 and 2, 5' V3 PvuII primer from reaction 1, and the 3' V3 XbaI primer from reaction 2 were used as substrate and primers in a third PCR amplification. The resultant amplified product included a PvuII to XbaI V3 loop containing fragment that carries the desired N-linked combination. Single mutants were used as substrate for the amplification of subsequent combinations of V3 N-linked mutants.

Figure 6:
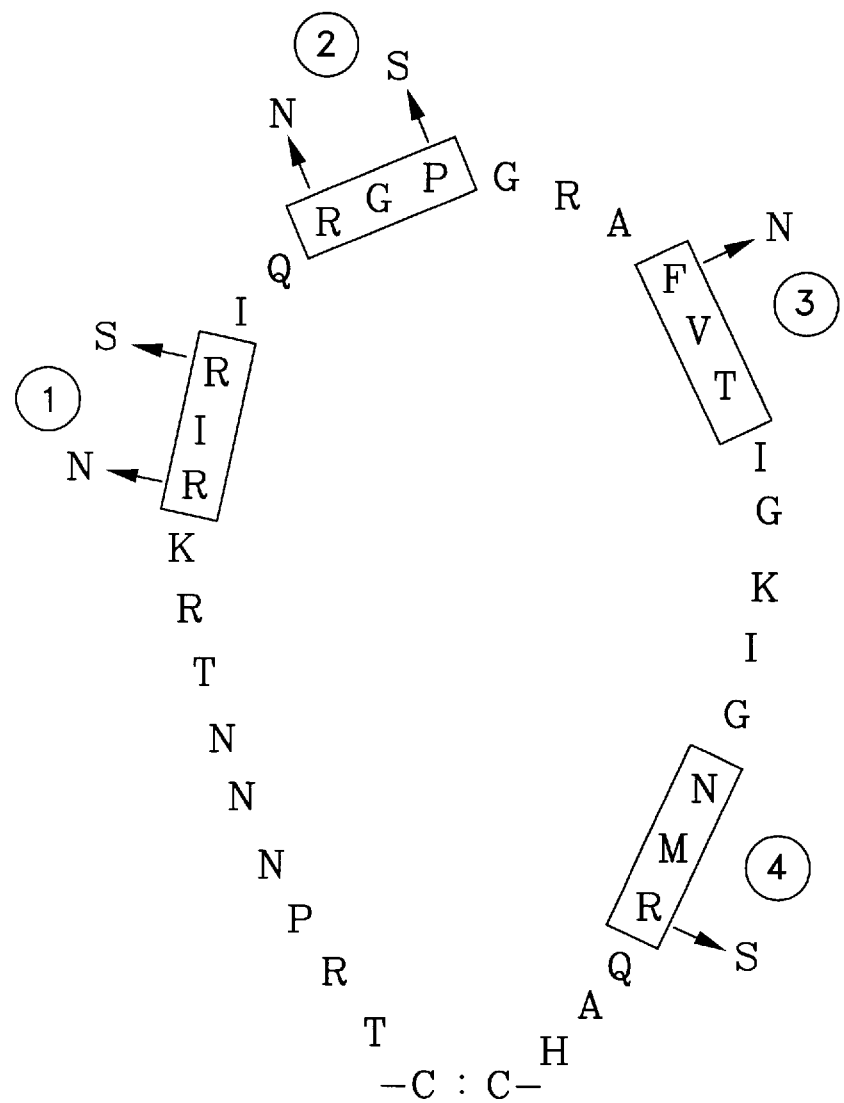
FIG. 6 is a schematic diagram of the HXB2 V3 loop of the gp120/160 envelope protein. Amino acid replacements that were performed by site-directed mutagenesis are illustrated. The various mutants are labeled: 1 (RIR); 2 (RGP); 3 (FVT); 4 (NMR). All of the mutations shown here were designed to generate consensus motifs that would direct N-linked glycosylation of proteins in the exocytotic pathway.

FIG. 6 shows the amino acid sequence of the V3 region of gp120/160 (SEQ ID NO:1) and the four N-linked Glycosylation Sites introduced into this region in accordance with this embodiment of the invention. These mutant sites are referred to herein for simplicity as mutants 1, 2, 3 and 4. Table 1 shows the PCR primers used in accordance with this embodiment of the invention to introduce the desired N-linked glycosylation signals for single and various multiple mutants. Table 1 also shows PCR primers for introduction of NotI sites as described elsewhere herein.

TABLE 1

| Mutant | Primer Sequence | SEQ ID NO.: |
|---|---|---|
| 5' 2 | TCCGTATCCAGAATGGATCAGGGAGAGCAT | 2 |
| 3' 2 | ATGCTCTCCCTGATCCATTCTGGATACGGA | 3 |
| 5' 3 | CCAGGGAGAGCAAATGTTACAATAGG | 4 |
| 3' 3 | CCTATTGTAACATTTGCTCTCCCTGG | 5 |
| 6' 1 | ATACAAGAAAAAACATCAGTATCCAGAGAG | 6 |
| 3' 1 | CTCTCTGGATACTGATGTTTTTTCTTGTA | 7 |
| 5' 2:1 | GTATCCAGAATGGATCAGGGAGAGCA | 8 |
| 3' 2:1 | TGCTCTCCCTGATCCATTCTGGATAC | 9 |
| 5' 2:3 | TCAGGGAGAGCAAATGTTACAATAGG | 10 |
| 3' 2:3 | CCTATTGTAACATTTGCTCTCCCTGG | 11 |
| 5' 1:2:3 | TCAGTATCCAGAATGGATCAGGGAGA | 12 |
| 3' 1:2:3 | TCTCCCTGATCCATTCTGGATACTGA | 13 |
| 5' Env-NotI | GGCAAGTGGTCAAAAGCGGCCGCTAC | 14 |
| 3' End-NotI | GTAGCGGCCGCTTTTGACCACTTGCC | 15 |
| 5' Env-NotI | CAGAGAGAAAAAAGATAAGCGGCCGCTGC | 16 |
| 3' Env-NotI | GCAGCGGCCGCTTATCTTTTTTCTCTCTG | 17 |

The mutagenized polynucleotides from Example 1 can be inserted into a cassette system for easy transfer into appropriate expression vectors, such as in Example 2.

EXAMPLE 2

Construction of pGEM 120 Cassette

Two intermediate plasmid cassettes were constructed to facilitate transfer of modified V3 domains. This was necessary since vaccinia expression vector pSC65 has inherent PvuII and XbaI sites which make it prohibitive for V3 PvuII-XbaI transfer. A SalI-NotI polylinker was ligated into SalI-PvuII digested pGEM-1. The gp120/160 sequence of pJJ25 was amplified using a 5' SalI primer spanning the start codon of gp160, and a 3' primer which includes an inframe stop codon at the 120/41 cleavage site as well as a NotI site positioned just proximal to the stop codon. This PCR product was digested with SalI and NotI and subcloned into SalI-NotI modified pGEM-1. The V3 minus gp120/160 envelope was sequenced and found to have two silent changes and two amino acid changes compared to the published HXB2 sequence. Ratner et al. *AIDS Res. Hum. Retroviruses* 7:615 (1991). This vector, pGEM-B2-120, was used to accept PvuII-XbaI digested N-link modified V3 fragments, and ultimate transfer of modified gp120/160 into a vaccinia expression vector.

Another method for constructing novel N-linked glycosylation signal motifs is shown below in Example 3.

EXAMPLE 3

A method for constructing nucleic acid sequences that encodes HIV-1 gp120/160 proteins bearing novel N-linked glycosylation signal motifs A polymerase chain reaction (PCR) protocol for site-directed mutagenesis was used to introduce N-linked glycosylation signals into the portion of the HXB2, HIV-1 genome that corresponds to the third hypervariable domain (the V3 loop) of gp120/160. The plasmid pMCII, which carries a full length infectious HXB2-like genome, was used as a template for the PCR mutagenesis. Complementary synthetic oligonucleotide primer pairs that carry mismatches designed to introduce the desired N-linked mutations were synthesized by Operon Technology Inc. Two partially complementary halves of the V3 region of plasmid pMCII were amplified by PCR using the conditions described in Example 1.

Example 3 above illustrates how the gene sequence encoding the V3 domain of gp120/160 can be altered to encode novel N-linked glycosylation signal motifs. Essential components of this approach include the use of a PCR based mutagenesis protocol and the use of plasmid cassettes that can receive mutated V3 domain polynucleotide sequences as restriction fragments.

Primers for PCR were designed and synthesized so that the three codons that encode the RIR amino acid triplet within the V3 domain of gp120/160 were omitted. These primers were used essentially as described under Example 3 to produce gp120/160 cassettes that have all of the gp120/160 coding sequence with the exception of the RIR amino acid sequence that is present in the wildtype sequence. We used the same approach that has been described previously to incorporate these modifications into recombinant vaccinia virus expression constructs. These constructs were then used to infect cells growing in culture as a means of producing recombinant gp120/160 glycoproteins having small deletions within the V3 domain. These same viral constructs were used to infect test animals so as to provoke an immune response against these recombinant gp120/160 glycoproteins.

EXAMPLE 4

A method of constructing a plasmid vector that can be used to accept wildtype and modified DNA fragments encoding the V3 domain of gp120/160

A modified plasmid vector was constructed to facilitate subcloning manipulations involving the PvuII to XbaI DNA fragments that encode the V3 domain of gp120/160 as described in Example ?. The use of this modified plasmid is necessary because the pSC65 vaccinia expression plasmid that would ultimately be used to receive the modified DNA fragments prepared as in Example 3, harbors undesired PvuII and XbaI restriction sites. Hence, the pSC65 plasmid cannot be uniquely cut with PvuII and XbaI in such a way as to appropriately receive the mutant V3 sequences as a PvuII-XbaII restriction fragment. The modified plasmid vector was prepared in two stages as follows. Plasmid pGEM1 (Promega) was cleaved with SalI and PvuII. The vector-containing fragment was then ligated to a synthetic SalI-NotI polylinker oligonucleotide. A separate manipulation was carried out on plasmid pJJ25 that harbors an NcoI to BamHI HXB2-like fragment containing a small PvuII-XbaI stuffer insertion. The gp120/160 sequence of pJJ25 was amplified using a 5'SalI primer that spanned the translational start codon of gp160, and a 3' primer that includes an in-frame stop codon at the gp120/160/41 cleavage site as well as a NotI site positioned just proximal to the stop codon. This PCR product was digested with SalI and NotI and subcloned into the SalI-NotI site of the modified pGEM1 plasmid. This plasmid, called pGEM-B2-120, was used to accept PvuII-XbaI DNA fragments bearing modified V3 region DNA sequences as prepared in Example 3 above. This then allows the entire gp120/160 coding sequence of mutant constructs that contain modified PvuII-XbaI inserts to be excised as a SalI-NotI fragment.

EXAMPLE 5

Construction of a plasmid that can accept wildtype and modified DNA fragments corresponding to the V3 domain, and which will reconstruct the full length envelope gene (gp120/41)

To incorporate V3 region site-directed mutants such as those described in Example 3 into the context of the gp160 gene sequence, the plasmid pGEM-B2-120 was modified to include additional gp160 coding sequences. This was done by creating a new plasmid in which the XbaI-NotI fragment of plasmid pGEM-B2-120 was replaced by a larger XbaI-NotI fragment that included DNA sequences that are downstream of the 120/41 cleavage site, and which are present in the gp160 coding sequence. To do this, the plasmid pMCII was used as the template for a PCR in which the 5' primer introduced a silent XbaI site at nts 7223–7228, and the 3' primer introduced a NotI restriction site just downstream of the gp160 stop codon. The 1 kb amplification product was then exchanged for the smaller XbaI-NotI fragment in the pGEM-B2-120 plasmid to create the new plasmid called pGEM-B2-160. Hence, by cleaving the pGEM-B2-160 plasmid with PvuII and XbaI and removing the stuffer fragment, it was possible to ligate in the PvuII-XbaI DNA fragments bearing mutated V3 domain sequences as described in Example 4.

The following Example shows that the mutants can be expressed.

EXAMPLE 6

A method of constructing a vector that directs expression of the N-linked gp120/160 mutant proteins in HeLa cells Mutated envelope gene segments were subcloned into a pSC65 vaccinia expression vector that had been modified by introduction of a synthetic SalI-NotI polylinker into the SalI-SmaI site of the plasmid. This plasmid harbors a synthetic early/late promoter and a copy of the lac Z gene located within a TK gene.

The selection of recombinant vaccinia virus has been described by Earl and Moss (Current Protocols in Molecular Biology, Greene Publishing and Wiley-Interscience. Supplement 15, Units 16.15–16.18), the disclosure of which is hereby incorporated by reference. Briefly, $1 \times 10^6$ CV-1 cells are infected with vaccinia viral strain WR at an MOI of 0.05. These cells are transfected two hours after infection with 10 to 20 ug of the vaccina expression plasmids containing the N-linked modified HIV-1 envelopes. Infected cells are pelleted, resuspended in 0.5 ml MEM, freeze thawed 3× and serially diluted to give single plaques in subsequent infection of Human TK- HeLa cells. These cells are overlain with soft agar in media containing 0.25 ug/ml of deoxy-bromo-uridine and incubated for 48 hours. A second soft agar overlay containing plaque media, 1/200 volume of 4% Xgal (Boehringer Mannheim) and 1/100 volume 10 mg/ml neutral red is applied. After overnight incubation recombinant candidates (i.e., TK- blue plaques) are selected, resuspended in 0.5 ml MEM, and processed through two additional rounds of plaque purification. Viral DNAs were sequenced to confirm the presence of the N-linked mutation.

Verification of recombinant virus expressing gp120 or gp120/41 was assessed as follows. Whole cell immunofluorescence using pooled sera to HIV-1, and a second FITC conjugated anti-human IgG was used to reveal the presence of membrane bound gp120/160/41 (i.e., 160 expressing constructs). An ELISA employing antigen capture using Ab to the carboxy terminus of gp120, pooled human sera to HIV-1, and FITC conjugated anti-human IgG was used to identify secreted gp120 or from both gp120/160 and gp120/41 expressing virus. In addition, presence of gp120/160, or gp120/160/41 will be confirmed by Western Blot. N-linked modified V3 proteins will be characterized as to their ability to bind to cellular and soluble CD4, 0.5β, a battery of diagnostic V3 antibodies, and anti gp41.

We verified the glycosylation status of the mutant gp120/160 proteins according to the methods described in the following two examples.

EXAMPLE 7

A method to verify the N-linked glycosylation status of gp120/160 proteins displaying mutant V3 domains.

Recombinant gp 120/160 proteins that are candidates for post translational addition of N-linked oligosacharides were tested for the presence of supernumerary carbohydrate moieties. The gp120/160 proteins in lysates of SupT1 cells infected with recombinant vaccinia virus (Example 6) were first enriched by lentil lectin affinity and then subjected to partial cleavage by V8 protease. The cleavage products were then electrophoresed on a 4–20% polyacrylamide gel in the presence of SDS, Western blotted and visualized with a V3 specific antibody. The peptide fragment derived from a protein displaying the wildtype V3 domain migrates with an apparent molecular weight of approximately 69 KDa. Non-glycosylated mutants are expected to exhibit a similar mobility. The presence of a carbohydrate moiety retards the migration of the protein fragment by an amount that corresponds to approximately 2 KDa in this assay. Our results indicate that mutants 1 (RIR) and 2 (RGP) show identical mobilities when compared with the wildtype V3 peptide fragment. Conversely, mutants 3 (FVT) and 4 (NMR) exhibit a slightly retarded mobility on the Western blot. These results are consistent with the presence of a supernumerary carbohydrate moiety in the V3 domain of mutants 3 and 4. Furthermore, this upward shift in the molecular mass of the peptide fragments derived from mutants 3 and 4 is abolished when the protein samples are pre-treated with a glycosidase. This scheme provides conclusive proof that two of the mutant V3 domains bear novel glycosylation modifications.

EXAMPLE 8

A Method to Verify the Functional Integrity of Recombinant gp120/160

We took advantage of the fact that native gp120/160 participates in target cell binding and entry to design assays to assess the functional integrity of the recombinant gp120/160 molecules. We have expressed the recombinant HIV-1 gp160 N-linked mutants in cells. An ELISA assay was used to test the interaction between these mutant proteins and a soluble CD4 receptor molecule. Concentrations of gp120/160 for each recombinant protein were determined by an antigen capture ELISA protocol using antibody to the C-terminus of gp160 (International Enzymes Inc., Fallbrook Calif.) and capture by soluble CD4. The CD4 binding index was calculated by taking the above ratio ([gp160 by C-terminal capture]/[gp160 by CD4 capture]) and dividing by the ratio determined for the wildtype. Results are shown in Table 2.

TABLE 2

| | V3 Specific Antibody ELISA | | |
|---|---|---|---|
| | | Antibody | |
| Mutant | 9284 | F58/H3 | 0.5β |
| WT | +++ | +++ | +++ |
| 1 | +++ | +++ | − |
| 2 | + | ± | − |
| 3 | +++ | +++ | − |
| 4 | +++ | +++ | ++ |
| 1:3 | +++ | +++ | ± |
| 1:4 | + | +++ | − |
| 2:4 | + | − | − |
| 1:2:4 | − | − | − |
| 1:2:3:4 | − | − | − |

*Relative binding to mutant proteins by antibodies compared to the wild type protein is calculated as $\frac{\text{measured concentration mutant}}{\text{measured concentration wild type}} \times 100\%$ as indicated as follows:

+++ > 90%, ++50–90%, +10–49, −1–9, no binding.

The results presented in Table 2 demonstrate that all of the proteins that harbored the N-linked site-directed mutations bound CD4. In this table, all of the results have been normalized to the level of binding that is observed for the wildtype gp160 glycoprotein. The mutant in position 3 showed the greatest reduction in CD4 binding. All of the other mutants are relatively close to the level observed with the wildtype envelope protein. This result prompted an investigation of the functional integrity of the mutants using an independent means of assessment.

We further analyzed the functional integrity of the N-linked gp120/160 mutants by testing the viability of recombinant HIV-1 genomes that harbored the N-linked mutations in the V3 domain of the gp120/160 envelope gene. All of the N-linked mutations were introduced into plasmids that carried complete HIV-1 genomes. These potentially infectious molecular clones were transfected into SupT1 cells. Infectious viability was determined by monitoring p24 expression. After the initial p24 spike, cell free supernatants were transferred to uninfected SupT1 and monitored again for p24 and syncytial production. All four of the single mutants are viable. Incorporation of multiple glycosylation signals into the V3 loop of gp120/160 rendered all virus constructs non-viable. Hence, the presence of a single glycosylation signal motif in the V3 domain of the gp120/160 protein does not disrupt the gp120/160 conformation to the extent that it compromises virus viability.

EXAMPLE 9

A method to verify that gp120/160 proteins bearing mutant V3 domains exhibit altered antigenic properties A Western blotting protocol was used to assess the antigenic profile of the mutant gp120/160 proteins. The panel of antibody reagents that recognized different epitopes within the wildtype HIV-1 V3 domain is represented on the right side of FIG. 7. The antigenic targets of these reagents are diagrammed below the V3 amino acid sequence, and include one or more of the sites within the V3 domain that have been altered by site-directed mutagenesis as described in Example 3.

It can be seen in FIG. 7 that mutant 1:2:3:4 was not recognized by any of the antibodies. Other single and multiple mutants showed varying reactivity with the various antibodies. The anti-gp41 antibody bound to all of the mutants. Thus, the foregoing example confirms that addition of N-linked glycosylation signals can alter the ability of antibody to bind to an immunodominant epitope.

Crude lysates of HeLa cells that had been infected with recombinant vaccinia virus constructs (Example 6) were used as the source of wildtype and mutant gp120/160 proteins for our antibody binding studies. High manose containing glycoproteins were enriched by affinity chromatography using a lentil lectin sephrose column. Bound glycoproteins were eluted from the column with α-methyl-D-manose. These proteins were then separated by polyacrylamide gel electrophoresis in the presence of SDS and Western blotted. These blots were then probed with the various antibody reagents to assay for the presense or absence of the various antigenic targets that are found in the wildtype gp120/160 molecules. Uniform sample loading was confirmed by the comparable anti-gp41 staining intensities for all samples. The absence of staining by any of the anti-V3 reagents must therefore result from the inability of the antibody to recognize the recombinant target, rather than by any loading artifact.

The presence of the epitope recognized by a particular antibody reagent is indicated by the presence of a stained band on the Western blot. The positive control wildtype gp120/160 is bound by all of the V3 specific antibodies as expected. Conversely, the antigenic character of the 1:2:3:4 mutant is quite different from that of the wildtype envelope molecule. This mutant does not display any of the wildtype epitopes that can be detected by our panel of antibody reagents. These results confirm the effectiveness of our approach to modify the antigenic structure of the gp120/160 glycoprotein.

Changing Native Charge

Another method of immunodampening an immundominant epitope is to change the native charge on the epitope. This can be accomplished through site-directed mutagenesis of the gene encoding the immunodominant epitope. For example, codons specifying charged amino acids can be changed to code for either an amino acid of the opposite charge or for a non-polar amino acid. Similarly, a codon specifying a non-polar amino acid can be changed to a polar amino acid of either positive or negative charge.

The approach of the examples described hereinabove in connection with the addition of N-linked glycosylation signals is sufficiently general that appropriately selected PCR primers can be used to introduce a variety of mutations into the V3 coding portion of the gp120/160 gene sequence. The amino acids that contribute to the overall net positive charge of the V3 domain can be substituted with amino acids that have either uncharged or acidic side chains. As one particular example, the RIR site-directed mutant shown in FIG. 6 involves the substitution of two positively charged arginine residue by uncharged asparagine and serine residues.

Antibody Masking and Immune Focusing

Still another approach at refocussing the immune response away from the immunodominant epitope involves masking of antibodies by binding of a moiety to that epitope. Antibodies irreversibly bound to cognate antigenic domains can mask targeted epitopes from being seen by B-cells. An immune response can be focussed to a more conserved domain like the gp120/160/CD4 binding domain by using such a strategy. For example, V3 specific antibody can be irreversibly crosslinked, and the complex presented as an immunogen. In addition, sCD4 irreversibly bound to gp120/160 can be used as a starting immunogen. Antisera raised to this complex can be irreversibly bound to gp120/160. This includes a battery of antibodies raised to non CD4 binding domains on the molecule. This complex in turn can be presented as an immunogen to raise antibodies against the CD4 binding domain.

Antibodies or other ligands irreversibly bound to cognate antigenic domains can mask the bound epitopes from immune surveillance. It may be possible to focus an immune response away from an immunodominant epitope like the V3 loop of of gp120/160 to a more conserved region of the molecule like the gp120/160/CD4 binding domain by using this strategy.

Antibodies, antibody fragments, antibody analogs or other ligands that can be irreversibly bound to cognate antigenic domains can mask the linked epitopes from immune surveillance. It may be possible to focus an immune response away from an immunodominant epitope like the V3 loop of gp120/160 in favor of more conserved regions of the molecule like the gp120/CD4 binding domain by using a strategy based on production and use of a masked immunogen.

EXAMPLE 10

A method for masking an immunodominant epitope by irreversibly binding a second molecule to that domain of the antigen A masked immunogen for HIV-1 gp120 is created as follows. Lentil lectin sepharose chromatography is first used to enrich gp120 from the supernatants of HeLa cell cultures that have been infected with wildtype HIV-1. Site-specific monoclonal antibodies that recognize epitopes within the V3 loop are then chosen. The antibody called 0.5β binds an epitope within the V3 loop that encompasses at least 14 amino acids. Appropriately buffered solutions of the 0.5β antibody and the partially purified gp120 are then combined and crosslinked according to the method of Titus et al., *J. Immunol.*, 138:4018–4022 (1987), the disclosure of which is hereby incorporated by reference. Following an appropriate reaction period, the sample is diluted and the reaction products separated by gel filtration chromatography. The column fraction that consists of a chemically crosslinked gp120/0.5β pair is isolated and dialyzed against an appropriately buffered saline-based solution. The crosslinked complex, in combination with an appropriate adjuvant can then be used in a standard immunization protocol.

Priming and Boosting with Masked Decotope

Yet another approach at immunodampening involves a primary immunization to native antigen. For example, animals can be primed with native HIV-1 envelope through infection with appropriately altered recombinant vaccinia. Animals can then be boosted with V3 altered gp120/160 to direct secondary response to other epitopes.

Insertion of Tolerated Sequences

Another approach that can be used to immunodampen the dominant epitopes encoded by pathogens is to substitute the amino acid sequence of that region of the antigen with a protein motif to which the human immune system is tolerant. For example, the native amino acid sequence in the V3 loop can be exchanged for a sequence that is tolerated by human B cells. This by definition, would include any linear human B-cell epitope. The objective of this approach is to create a mutant form of the pathogen's antigen in which a segment of the pathogen's antigen is replaced by an amino acid sequence that displays human character. In this way the human immune system will be prevented from mounting a strong immune reaction against that region of the pathogen's antigen that would otherwise serves as a dominant epitope.

EXAMPLE 11

Construction of a recombinant vaccinia virus vector that expresses gp120/160 protein in which the V3 loop is substituted by a tolerized human epitope A chimeric immunodampened antigen in which the immunodominant domain of the native antigen is replaced by a tolerized human sequence is constructed as follows. We begin by isolating a DNA restriction fragment that encodes a stretch of amino acids corresponding to a polypeptide against which the human immune system ordinarily does not respond. The amino acid sequence of the human IgM CH3 domain is used for this purpose. The complete amino acid sequence of this domain is available in Kabat, Sequences of Proteins of Immunological Interst (1991). The DNA restriction fragment is isolated from a nucleic acid clone if conveniently disposed restriction sites are available. Alternatively, a PCR protocol is used to introduce appropriate restriction sites into such a nucleic acid sequence. Such a DNA fragment is then ligated into the pGEM-B2-120 and pGEM-B2-160 plasmids that we have described earlier in this application. Special attention is paid to preserve the translational reading frames of the gp120/160 and the grafted human antigen sequences. In so doing, modified gp120 and gp160 gene cassettes that bear substitutions of the tolerized human sequence in place of the wildtype V3 domain are created. The SalI-NotI restriction fragments from these cassettes are then transferred to the modified pSC65 vaccinia vector described hereinbelow in Example 6. These gene sequences are subsequently incorporated into viable virus constructs according to standard techniques.

Although the following procedures are carried out using guinea pigs as test animals, those of ordinary skill in the art can readily adapt a similar approach that can be applied to human subjects.

Thrombin Cleavage

Thrombin uniquely cleaves HX10 gp120/160 into two fragments cutting between amino acids R and A in the V3 loop. Clements et al., *AIDS Res. Hum. Retroviruses,* 7:3–16 (1991). Neutralizing antibodies (110.5 0.5 B) whose binding domain includes the above amino acids will not bind to the digested loop. Other V3 binding antibodies whose recognition sequence remains linearly intact still bind the cleaved loop (9284). However, prolonged treatment with Thrombin cleaves at secondary sites, causing some destruction of the 9238 site, as well as other possible cleavage sites elsewhere. Thus, controlled cleavage with thrombin will remove some of the neutralizing antigenicity of the V3 epitope.

Deletion

The HIV-1 env gene is clustered into five major hypervariable (V) regions interspersed between five constant (C) domains, giving the pattern C1-V1-V2-C2-V3-C3-V4-C4-V5-C5. Coffin hypothesized that the variable domains may exist in such a way that loops in the structure of gp120/160 can occur without interfering with the structural and functional nature of the molecule. This implies that gp120/160 binds to CD4 independent of the sequence heterogeneity of the variable domains. In addition, the variable domain of gp120/160 may be responsible for the antigenic variation extant between viral strains by diverting the immune response away from the more conserved domains. To test this hypothesis, Haigwood et al., supra, systematically deleted the variable regions of SF gp120/160 and expressed these deleted proteins in yeast. They hypothesized that using these deletants as immunogens might unmask more conserved epitopes. These studies were done with denatured, non-glycosylated versions expressed in yeast, and failed to elicit a more conserved neutralizing response. In addition, none of the deletion variants tested in this study bind to CD4. This may indicate the necessity to keep the envelope glycoprotein in a native state to maintain immunogenicity to the gp120/160/CD4 binding domain as the authors suggest, or the glycosylated version is in a non-native conformation. Independent work by others suggests that hypervariable regions of gp120/160 are not required for binding to CD4, since proteins from deletion mutants removing variable domains V1, V2 and V3 still bind to CD4 with high affinity. Although binding to CD4 was apparently uninterrupted, this deletant protein which still carries V4 and VS hypervariable domains which are required for CD4 binding did not bind go antisera raised to gp120/160. This is surprising, since Chang reported low affinity antibodies are raised to the gp120/160/CD4 binding domain. These data, therefore, suggest that V4 and V5 are either non-immunogenic domains, or more likely, the native conformation of the protein has been altered by the Deletions and the immune sera cannot recognize the deleted protein. Regardless, using this as an immunogen holds some promise, since the immune response may be directed to a potentially more conserved gp120/160/CD4 binding domain.

G. Vaccines

As will be appreciated from the foregoing discussion of various immunodampening techniques, we have used as a model system of our vaccination approach, the immunodampening of the immunodominant V3 loop of gp120/160 of HIV-1. However, as will also be readily appreciated by one having ordinary skill in the art, the approach can be readily adapted to other pathogenic organisms in accordance with the disclosure herein provided. Accordingly, the development of effective vaccination formulations and protocols is described below in connection with an HIV-1 vaccine. This description is provided solely to be exemplary, rather than to limit the application of the invention to any particular pathogenic organism.

The most effective design of an HIV-1 vaccine will avail itself of the few critical features of the virus that make it such a successful pathogen. Preventing the HIV-1 virus from deceiving the immune system in the first place represents a major advance in this regard. Accordingly, we have produced a gp120/160 immunogen in which the immunodominant epitope has been immunodampened.

The survival strategy that seems to have been adopted by the HIV-1 pathogen depends partly on the display of a dominant, virally encoded epitope that is subject to antigenic variation.

During the course of HIV-1 infection, the lag period between the time of infection and the manifestation of the immune response affords the virus an opportunity to replicate its genome using an error prone reverse transcriptase. This in turn allows for the emergence of a subpopulation of closely related but neutralization resistant variants. These variants not only escape the effects of neutralizing antibodies but, as a result of their antigenic similarity to the parent virus, continue to stimulate the initial immune response even though the antigenic character of the decotope has been altered. The net effect of this phenomenon is to lock in a directed, immuno-stimulatory response which, through cross reactivity, continues to produce immune effector responses to the earliest viral phenotype. Thus, an immunodominant decotope functions to decoy the immune system away from responding to more conserved and potentially broadly neutralizing domains. This strategy is critical for the continued pathogenesis by HIV-1.

The third hypervariable domain (V3) of the gp120/160 envelope glycoprotein represents an immunodominant epitope of HIV-1 that is the principal target for neutralizing antibodies. This domain, despite its variable character, exhibits some conserved structural features. The V3 loop is typically 35 amino acids in length and is bounded by 2 cysteine residues that are believed to form a disulfide bridge. The V3 loop has an overall positive charge and has a computer predicted B turn beta sheet in what is believed to be the apex of the loop.

A comparison of the protein sequences for different HIV-1 isolates indicates the virus can tolerate considerable amino acid sequence variability in the V3 domain of gp120/160. This ability to tolerate sequence changes in the immunodominant epitope of the virus without compromising viability is directly related to escape from the neutralizing phenotype. Antibodies that recognize different V3 domains exhibit a type specificity toward the immunizing domain. For example, antibodies raised to V3 peptide of a given strain neutralize that strain, but in many cases, fail to neutralize viruses that display alternative V3 epitopes. Although different V3 specific antibodies appear later in the course of infection, they do not reach the high titer that characterized the V3 specific antibodies during the early stages of the infection. Consequently, this late humoral and/or cell mediated response directed against the variant V3 epitope may be insufficient to hold the cognate viral population in check.

It is highly unlikely that all of the gp120/160 structure is as plastic as the V3 domain. Functional requirements for the gp120/160 molecule that include the ability to carry out target cell binding and entry are likely to impose structural constraints. The CD4 binding domain of gp120/160 is one example of a site that is likely to exhibit a strong conservation of structure. Antibodies have been isolated from AIDS patients demonstrating that the gp120/160/CD4 binding domain is immunogenic. In spite of this fact, antibodies to the gp120/160-CD4 binding domain are in much lower titer relative to anti-V3 antibodies. Thus, it is a tenable hypothesis that HIV-1 has invested part of its genomic content into a strategy which misdirects the host's immune response toward a decoy epitope and away from more structurally conserved functional domains.

In contrast to an immune response that is mounted against a variable region epitope like V3, we have discovered that a response to more conserved epitopes is significantly more likely to limit dissemination of the virus. Most of the neutralizing response to HIV-1 is directed toward the V3 domain and the CD4 biding domain. To date, vaccine attempts have only been able to withstand homologous challenges. This strongly suggests the immune response is directed toward a dominant variable epitope that distinguishes the structure of the immunizing strain and the challenge virus. The most likely candidate for this variable epitope is V3 on the gp120/160 molecule.

Hence our method can be used to attenuate the strong humoral and/or cell-mediated immune response that is ordinarily directed against the immunodominant V3 domain of the gp 120 envelope glycoprotein of wildtype HIV-1 isolates. Our approach involves modification of the antigenic structure of the V3 domain for the purpose of reducing its immunogenicity. The object of this approach is to enhance the humoral immune response against other epitopes on the gp120/160 molecule.

B cells respond to antigen through a T cell dependent or T cell independent pathway. In either case, the initial interaction between B cell receptor and cognate antigenic epitope results in proliferation and clonal expansion, affinity maturation of antibody, and finally, in high affinity, high specificity, antibody production. We propose to block the initial interaction between gp120/160-V3 epitope and its cognate B cell clone. However, at the same time other B cell epitopes to gp120/160, those whose structural integrity V3 specific clonal expansion, and allow the expansion, affinity maturation, and specific antibody production to other B cell epitopes on the molecule.

One method to accomplish expression of the recombinant gp120/160 protein molecules in mammalian cells makes use of a vaccinia virus expression system, as described above in Example 6. Among the features of this expression system is the fact that recombinant proteins can be produced in milligram quantities. These proteins are then available for biochemical studies, and for use as immunogens.

We foresee the use of dampened immunodominant epitopes as a novel vaccine strategy. Since different routes of immunization can selectively stimulate particular branches of the immune system, individual vaccines based on the technology described here may require different routes of administration. For example, a vaccine delivery system in which the production of neutralizing antibodies is emphasized may not be the method of choice if the pathogen in question is best combatted by a cellular immune response. This implies that a range of delivery systems should be tested for each new application of this vaccine technology. Possible routes of administration of the immunogen include, but are not limited to: inoculation by eye drops or sprays; by nasal spray or inhalation of aerosols; by ingestion; by subcutaneous, intradermal or intramuscular injection; by infection with recombinant virus vectors or by injection of naked DNA that directs gene expression once incorporated into host cells. The following example illustrates one of the ways that recombinant vaccinia virus and purified recombinant subunit proteins might be used in a human vaccination protocol. This example is not meant to represent the only means of vaccinating humans or other mammals with recombinant agents based on immunodampened, dominant epitopes.

EXAMPLE 12
Use of recombinant virus and gp120/160 bearing modified V3 domains as immunogens in a vaccine protocol Human subjects at risk of exposure to HIV-I were injected subcutaneously with $10^7$–$10^{10}$ pfu of the live recombinant vaccinia virus (Example 6) that had been propagated in HeLa cells and subsequently purified by sucrose density gradient banding. The virus preparations were exhaustively dialyzed against cold isotonic saline buffer prior to being titered. A second injection of the same live virus was administered 4 weeks later. This injection was given in the same location as the first inoculation. A subunit boost of purified recombinant gp 120/160 protein was then given in order to enhance the production of neutralizing antibodies, as described by Hu et al., *AIDS Res. Hum. Retroviruses* 7:615 (1991), the disclosure of which is hereby incorporated by reference. In addition to a crude purification of the recombinant glycoproteins by lentil lectin affinity chromatography, the injected proteins were also purified to near homogeneity by affinity chromatography using an immobilized anti-gp41 monoclonal antibody. The subunit proteins, that had been dialyzed against cold phosphate buffered saline were diluted to a final concentration range of 10–1000 μg/200 μl, and injected intramuscularly together with either complete Freund's, or ISCOM (Morein, *Immunol. Lett.* 25:281–83 (1992)) adjuvants. The development of neutralizing antibody titers were assayed by the method of Nara et al. (*AIDS Res. Hum. Retrovirus,* 3:283–302 (1987)).

Although the following procedures were carried out using guinea pigs as experimental animals, a similar approach would be applied to human subjects.

EXAMPLE 13
Development of a vaccination protocol using recombinant vaccinia virus and detection of a humoral immune response We routinely use a two part vaccination protocol that elicits an HIV-1 neutralizing antibody response in test animals. First, we inject guinea pigs subcutaneously with $10^7$–$10^8$ plaque forming units (pfu) of live recombinant gp120/160 expressing vaccinia virus. A second injection of the live virus is given approximately four weeks later. The effectiveness of this infection is evidenced by the appearance of small lesions at the site of injection. Next, we give the animals a single boost of the subunit immunogen by injecting 10 μg of lentil lectin sepharose purified wildtype or recombinant gp120/160 proteins.

We quantitated the humoral immune response as the extent to which a serum sample could be diluted and still neutralize 90% of an in vitro infection of cells with the wildtype HIV-1. Table 3 presents the serum titers from pairs of guinea pigs that had been infected with the recombinant vaccinia virus bearing the site directed mutations shown in FIG. 6.

TABLE 3

| Virus Neutralization Assay | |
|---|---|
| Antiserum | Neutralization Titer |
| WT | >32 |
|  | 32 |
| 1 | 32 |
|  | 8 |
| 2 | 8 |
|  | >32 |
| 3 | 16 |
|  | 32 |
| 4 | 32 |
|  | 32 |
| 1:3 | 32 |
|  | 32 |
| 1:4 | 8 |
|  | 8 |
| 2:4 | >32 |
|  | >32 |
| 1:2:4 | 8 |
|  | >32 |
| 1:2:3:4 | 8 |
|  | >32 |
| vaccinia virus control | No effect |
|  | No effect |

Serum samples were drawn and titered at two weeks post-infection. While the infection of test animals with a vaccinia control failed to elicit antibodies that neutralized HIV-1 infection in vitro, infection with recombinant virus 1:2:3:4 elicited neutralizing antibody titers that were moderate in one animal, and equivalent to our positive controls in the other animal. This result is significant in view of the fact that earlier results demonstrated the mutant V3 domain of the 1:2:3:4 recombinant exhibits a very different antigenic profile when compared with the wildtype. Given the weak antigenic relationship between the wildtype and the 1:2:3:4 mutant gp120/160, the results presented in Table 3 are consistent with a senario in which the humoral immune response against the immunodampened mutant has been redirected from the immunodominant V3 loop to more conserved epitopes that are present on both the wildtype and on the mutant gp120 molecules.

---

What is claimed is:

1. An immunogenic composition, comprising:

a modified form of a native antigen of a pathogen, the native antigen having disposed at a position thereon an immunodominant epitope comprising a plurality of amino acids, said modified form of the native antigen having a modified epitope at the position of the immunodominant epitope of the native antigen, said modified epitope having been immunodampened so as to substantially redirect an immune response away from the modified epitope and toward a different part of said modified form of the native antigen; and a pharmacologically acceptable carrier.

2. The composition of claim 1, wherein said modified form of the native antigen has a modified amino acid sequence that includes one or more N-linked glycosylation signals not present in the native antigen.

3. The composition of claim 1, wherein said carrier comprises a pharmacologically acceptable saline buffer.

4. The composition of claim 1, wherein said modified epitope has been immunodampened by addition of carbohydrate moieties.

5. The composition of claim 1, wherein said modified epitope is immunodampened by an alteration of amino acids.

6. The composition of claim 5, wherein said alteration of amino acids comprises an amino acid substitution.

7. The composition of claim 5, wherein said alteration of amino acids produces an altered set of amino acids against which a humoral response is not substantially produced in a human.

8. The composition of claim 7, wherein said altered set of amino acids comprise a linear human B-cell epitope.

9. The composition of claim 5, wherein said immunodominant epitope has a native charge and said modified epitope has a modified charge that differs from the native charge of the immunodominant epitope.

10. The composition of claim 5, wherein said alteration comprises deletion of one or more amino acids.

11. The composition of claim 1, wherein said immunodominant epitope includes a binding site for at least one other molecule, and wherein said composition additionally comprises said at least one other molecule irreversibly bound to said immunodominant epitope.

12. The composition of claim 11, wherein said other molecule comprises an antibody directed against said immunodominant epitope.

13. The composition of claim 1, wherein said pathogen is HIV-1.

14. The composition of claim 13, wherein said native antigen is gp120/160.

* * * * *